(12) United States Patent
Lindeman

(10) Patent No.: US 7,827,868 B2
(45) Date of Patent: Nov. 9, 2010

(54) APPARATUS FOR A CAM-BASED JACK ASSEMBLY FOR USE IN MATERIALS, TESTING MACHINES AND AN ACCOMPANYING METHOD FOR USE THEREWITH

(75) Inventor: Norman A. Lindeman, Sand Lake, NY (US)

(73) Assignee: Dynamic Systems, Inc., Poenstenkill, NY (US)

( * ) Notice: Subject to any disclaimer, the term of this patent is extended or adjusted under 35 U.S.C. 154(b) by 36 days.

(21) Appl. No.: 12/313,432

(22) Filed: Nov. 20, 2008

(65) Prior Publication Data
US 2009/0139344 A1 Jun. 4, 2009

Related U.S. Application Data

(60) Provisional application No. 61/004,825, filed on Nov. 30, 2007.

(51) Int. Cl.
*G01B 5/30* (2006.01)
(52) U.S. Cl. .......................................... 73/859; 73/760
(58) Field of Classification Search ............ 73/760–860
See application file for complete search history.

(56) References Cited

U.S. PATENT DOCUMENTS

| 1,872,047 | A |   | 8/1932  | Templin |             |
|-----------|---|---|---------|---------|-------------|
| 2,350,577 | A |   | 6/1944  | Vordahl | 73/51       |
| 2,634,487 | A |   | 4/1953  | Rogers  | 24/248      |
| 3,247,565 | A |   | 4/1966  | Griffin | 24/263      |
| 3,403,549 | A |   | 10/1968 | Griffin | 73/103      |
| 3,486,372 | A |   | 12/1969 | Lange   | 73/103      |
| 3,838,596 | A | * | 10/1974 | Neuenschwander | 73/816 |
| 4,313,337 | A | * | 2/1982  | Myint   | 73/12.13    |
| 4,537,080 | A | * | 8/1985  | Christiansen | 73/857 |
| 5,202,542 | A |   | 4/1993  | Ferguson | 219/50     |
| 6,629,466 | B2| * | 10/2003 | Grote et al. | 73/857 |
| 2002/0166387 | A1 | * | 11/2002 | Grote et al. | 73/857 |

FOREIGN PATENT DOCUMENTS

GB 617428 2/1949

* cited by examiner

*Primary Examiner*—Max Noori
(74) *Attorney, Agent, or Firm*—Michaelson & Associates; Peter L. Michaelson

(57) ABSTRACT

A jack assembly, for use in a materials testing system, utilizes both a cam and a resilient push block. The cam, having an progressive eccentric, is situated between the push block and a jaw housing and located partially within a corresponding shallow channel in each such that both channels effectively straddle the cam. The channels accommodate axial rotation of the cam. The push block is formed of a material with an appropriate modulus of elasticity such that bending moments, particularly at ends of the push block and resulting from axial rotation of the eccentric to its top dead-center position, cause the channel in the push block to elastically deform and increasingly and sufficiently deflect against and around the eccentric, thus increasingly pinching the eccentric and securely locking the cam, push block and specimen grip in their proper positions.

37 Claims, 7 Drawing Sheets

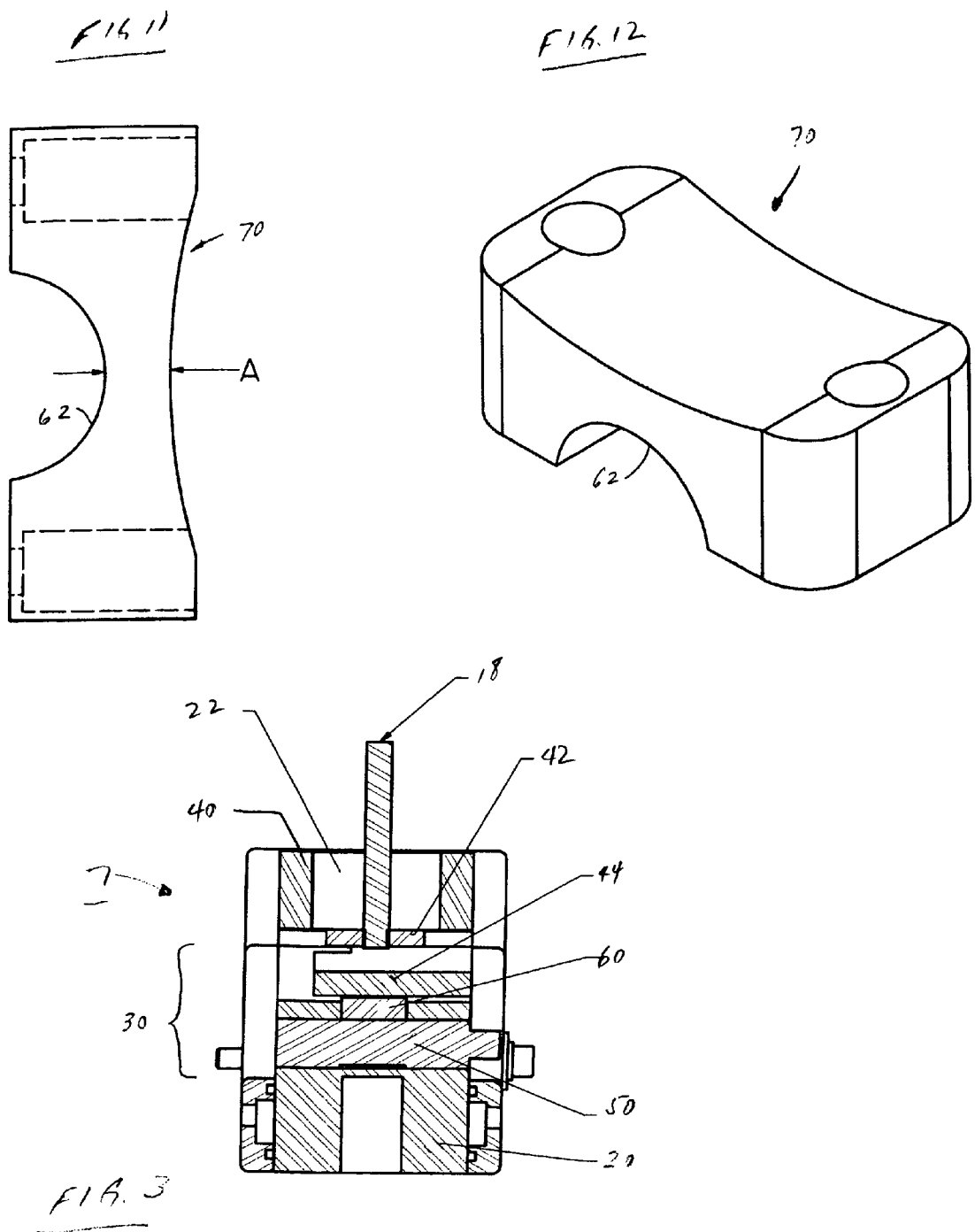

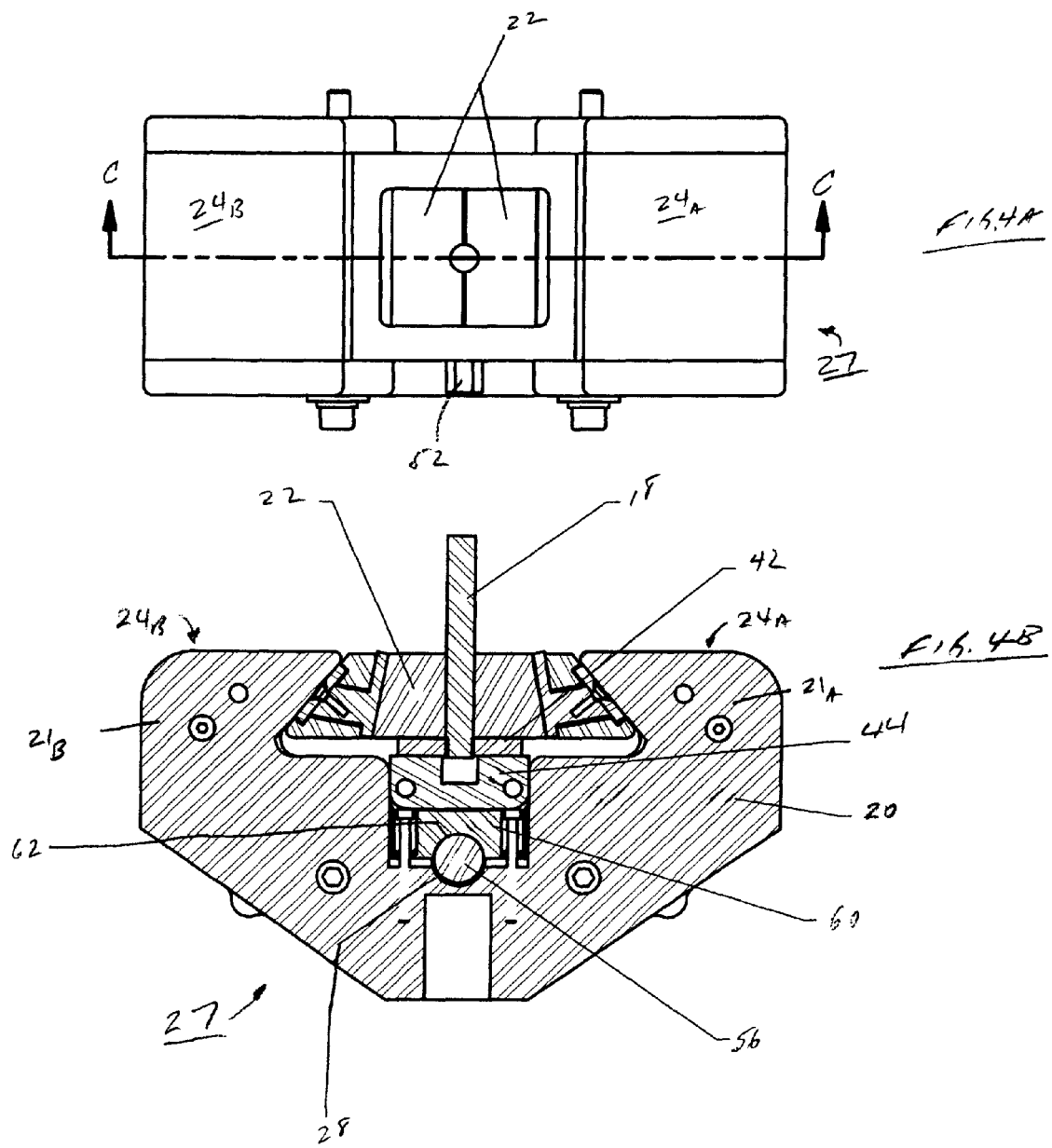

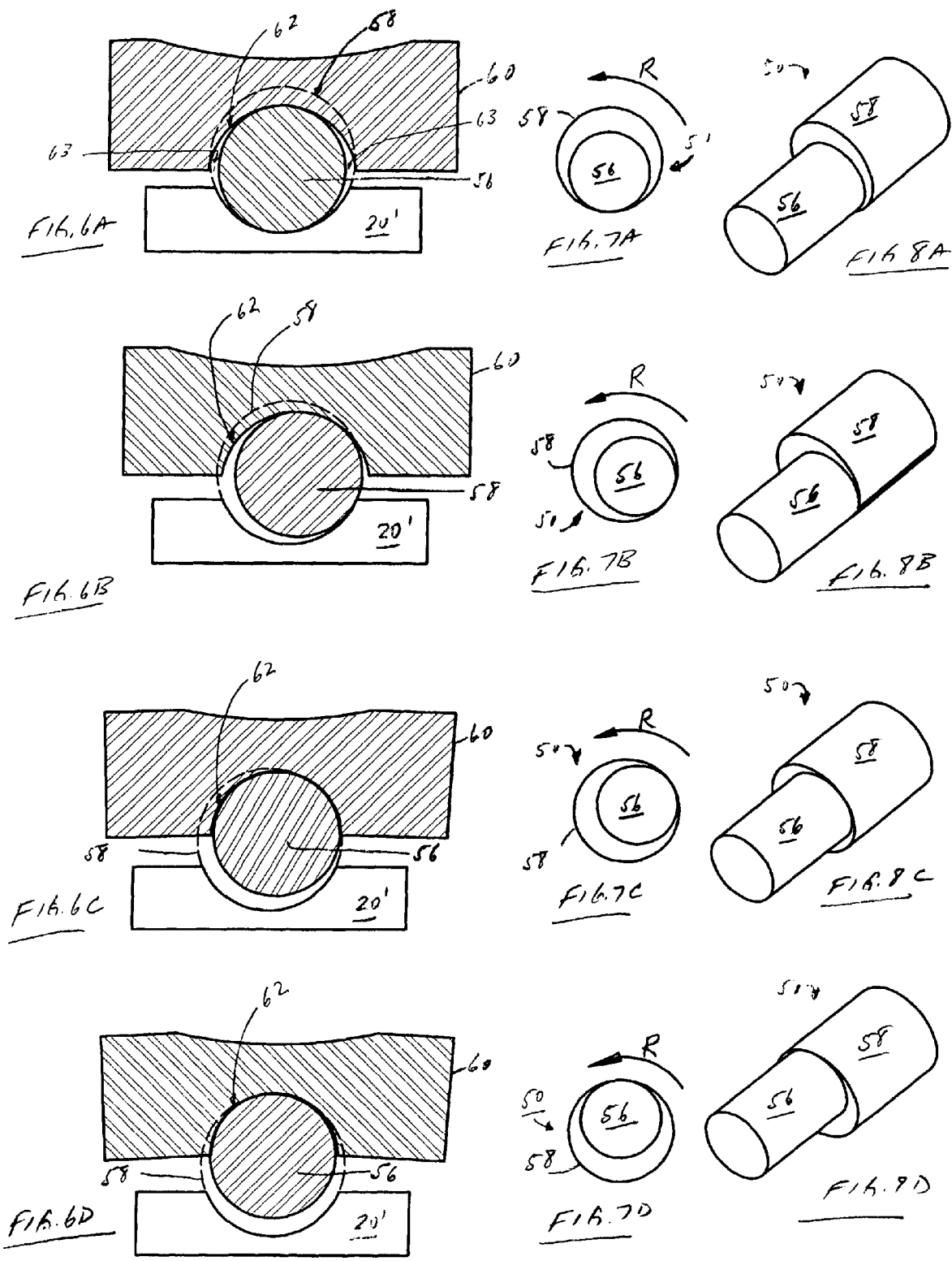

APPARATUS FOR A CAM-BASED JACK ASSEMBLY FOR USE IN MATERIALS, TESTING MACHINES AND AN ACCOMPANYING METHOD FOR USE THEREWITH

CLAIM TO PRIORITY

This application claims priority of my co-pending United States provisional patent application entitled "Cam Jack System for Use in Materials Testing Machines", filed on Nov. 30, 2007 and assigned Ser. No. 61/004,825; and which is incorporated by reference herein.

BACKGROUND OF THE DISCLOSURE

1. Field of the Invention

This invention pertains to apparatus and an accompanying method for a jack assembly that secures a grip and specimen held thereby into proper position in a jaw of a materials testing machine and applies suitable pressure and restraint to the grip during mechanical testing. The present invention is well suited for use in a variety of different mechanical and thermo-mechanical material testing machines, including those which provide compressive and tensile testing of a mechanical test specimen.

2. Description of the Prior Art

Conventional materials testing machines utilize a wide range of screw jacks, wedge plates and other types of jack assemblies in order to secure a grip, as it holds an end of a specimen under test, in proper position in a jaw during a mechanical test.

In such a machine, typically a known and controlled compressive and/or tensile force is applied, often under computer control and as defined by a so-called "test program", to one of two grips that hold the specimen and thus deform the specimen under predefined test conditions. Often, a test program may encompass applying a series of such forces—tensile and/or compressive, i.e., commonly referred to "hits", to the specimen to increasingly deform it. Dilation and/or other physical measurements are typically made of the amount of resulting deformation as or after each hit is made to the specimen. In a thermo-mechanical material test system, the specimen may be controllably and self-resistively heated, such as through serial passage of electrical heating current through the jaws and specimen, before, simultaneously with or after each such hit and as defined in the test program. Such systems are exemplified by the GLEEBLE dynamic thermo-mechanical material test systems presently manufactured by Dynamic Systems, Inc. of Troy, N.Y., which is the present assignee (GLEEBLE being a registered trademark of Dynamic Systems, Inc.).

Generally speaking, cams have been previously used to apply pressure to a component in a variety of machines. However, cams have traditionally not been used as a component of jack assemblies used in materials testing systems for the simple reason that a cam has a tendency to loosen unless the cam is jacked past its center position, i.e., rotated "over-center". In such a testing system, a mechanical force, generated through, e.g., a rod of an external servo-controlled hydraulic piston attached to one of the grips, the other grip often being secured in a fixed position, must be consistently applied up to a peak value through the one jaw and grip to the specimen end to produce each hit. If a cam were to be used in a jack assembly to properly hold that one grip in its corresponding jaw, a problem arises in that once the cam were to be rotated over-center to lock its grip in place, a mechanical force applied by that cam alone onto that grip decreases from its peak value that arises at a top dead center position of the cam. Consequently, once the cam would be turned over-center, that force applied by the cam decreases from its peak value applied at the top dead center position of the cam, thus reducing the lock force holding the grip in position during each subsequent hit, thus potentially allowing some specimen movement which, in turn, might inject some unwanted artifact into the resulting amount of deformation arising from that hit. Such a result may be problematic. Further, the externally generated forces required to deform the specimen during each hit are rather large and must be transmitted through the jack assembly and maintained on the specimen without the jack loosening throughout any of the hits that occur during an entire test program.

U.S. Pat. No. 3,403,549 (issued to A. G. Griffen on Oct. 1, 1968) appears to disclose the use of a cam as a component of a grip used in a materials testing machine. There, the cam acts as a pivot pin for a lever arm for moving jaw members backward in order to open two wedge grips to insert a test specimen therebetween. The cam is apparently not used to apply pressure in order to lock the jaw members into a closed position to grip the specimen.

Nevertheless, using a cam in a jack assembly would be advantageous because a resulting assembly would be capable of generating more force than would a similarly-sized screw-type jack assembly. In that regard, if a user were to manually apply torque to a cam-based jack assembly to generate a given mechanical force to lock the cam into position, a significantly higher amount of torque would need to be applied to the screw-type jack to generate the same amount of force. Unfortunately, a screw that could withstand that much torque would likely be too large to comfortably fit within a jack assembly used in a materials testing system, and hence, in that case, would render a screw-type jack assembly impractical.

Consequently, a yet unmet need exists in the art for a cam-based jack assembly, particularly suited for use in a materials testing system, that will rigidly hold a specimen grip in position in a jaw housing during entire test programs but which does not need to be jacked over-center.

SUMMARY OF THE INVENTION

My inventive apparatus for a jack assembly, particularly though not exclusively suited for use in a materials testing system, utilizes both a cam and a resilient push block member which abuttingly mates with the cam and, in so doing, advantageously overcomes the deficiencies in the art.

In accordance with my inventive teachings, the cam is formed to contain, in series, an upper circular cylinder, a progressive eccentric, with a predefined raising rate based on its axial rotation, and a lower circular cylinder. The eccentric is interposed between and sandwiched by the push block and the housing, each of which has a corresponding shallow channel with a generally semi-circular cross-section to accommodate the eccentric and its axial rotation. The push block is mechanically connected, via intermediate mechanical components, such as here a spacer and jam nut, to an underside of a specimen grip. Preferably, the cam is machined or otherwise formed from a single unitary piece of material.

As the cam rotates, about its longitudinal axis (i.e., its centerline, readily apparent though not specifically shown), into its top dead-center position relative to the push block, such as through a user simply manually rotating the cam through a suitable wrench or handle connected to a mating head of the cam, the eccentric, given its cam profile, will abut against and exert an increasing amount of force against the push block until that top dead-center position is reached at which point maximum force will be exerted by the eccentric onto the push block. The push block, being a laterally oriented, approximately rectangularly-shaped block is mounted at each of its ends to, e.g., the spacer, with its channel oriented transversely along its mid-span, substantially equidistant from its two ends. As the eccentric is rotated to increasingly push against the push block, bending moments are produced along the push block. The push block is fabricated out of an appropriate material, with a sufficiently high modulus of elasticity as compared to that of the entire cam and jaw housing, such that the bending moments applied particularly at and near two ends of the push block cause the channel in the push block to elastically deform and increasingly and sufficiently deflect against and around the eccentric section of the cam, thus increasingly bending around and pinching that section and securely locking the cam into position. As the deflection increases, contact surface area between the push block and a face of the eccentric similarly increases which, in turn, advantageously increases a resulting frictional force between the two. Once full torque is applied to the cam to place it in its top dead-center position, the push block will not only sufficiently and maximally deflect to appropriately pinch the eccentric and lock the cam in place but also the push block will simultaneously act as a spring to maintain a constant force on the specimen grip to also securely lock that grip and its specimen in place in the jaw.

The material of the push block is selected to have a sufficient modulus of elasticity that is a compromise value, namely, on the one hand, to sufficiently deflect around and pinch the eccentric at top dead-center positioning of the cam but also, on the other hand, to provide sufficient rigidity to withstand and transmit externally applied deforming forces for each "hit" through the jaw housing to the grip and specimen without the cam appreciably absorbing those forces and deforming as a result.

In accordance with a preferred embodiment of the invention, the jaw housing is simplistically-speaking generally a V-shaped block having two upwardly extending legs. Each leg has, at its distal end, an inwardly-oriented lateral projection such the projections of both legs effectively oppose each other. Each projection has an inclined face sloping back down to the leg itself, thus forming a pair of opposing inclined faces. The specimen grip is shaped in the form of two outwardly-facing wedges with a specimen anvil, illustratively formed of a pair of wedge grips, situated therebetween. Each of the wedges on the specimen grip has an inclined face complementary to one of the inclined faces on the jaw housing. The specimen grip is placed within the jaw housing such that each of its outwardly inclined wedges abuttingly mates and slides against an inclined face of a corresponding one of the projections. The specimen is typically a relatively short bar that is either circularly or rectilinear in cross-section.

The inventive jack assembly is situated in a space in the jaw housing and extends outward such that the spacer connected to the push block abuts against a bottom edge of the grip. Once an end of the specimen is properly secured in the anvil in the specimen grip, and the grip is appropriately placed in the jaw housing such that each of its inclined faces abuttingly engages with a corresponding one of the complementary faces of the housing, then the jack assembly is appropriately set by rotating the cam from its initial angular position (at which it applies no force to the push block) into its top dead-center position (at which it applies maximal force). This cam rotation expands the length of the jack and thereby exerts a sufficient continuous mechanical force, via the spacer, against the grip, through increasing frictional forces caused by relative sliding movement of abutting faces of a wedge effectively formed by each pair of complementary inclined faces of the jaw housing and the grip as they are forced towards each other, that locks the specimen grip into its proper position in the jaw housing.

As a result of increased force produced by the cam and the deflection of the resilient push block against the eccentric which, in turn, inhibits further rotational movement of the cam, advantageously, the cam will not "back off" its top dead-center position during its subsequent use during a mechanical test program that involves a succession of hits, and thus will securely hold the specimen in a proper fixed position relative to the jaw housing throughout the test program. This, in turn, will substantially, if not totally, eliminate artifacts in mechanical test results which might otherwise arise from unwanted specimen movement during the test program resulting from unwanted loosening of a conventional screw-type jack assembly.

BRIEF DESCRIPTION OF THE DRAWINGS

The teachings of the present invention can be readily understood by considering the following detailed description in conjunction with the accompanying drawings, in which:

FIG. 3 depicts a cross-sectional view of jaw 27 taken along lines B-B shown in FIG. 2A;

FIG. 4A depicts a top view of jaw 27 shown in FIG. 2A;

FIG. 4B depicts a cross-sectional view of jaw 27 taken along lines C-C shown in FIG. 4A;

FIGS. 6A, 6B, 6C and 6D respectively depict a side view of cam 50, specifically showing cylindrical section 58 and eccentric 56, and abutting simplified jaw housing 20' and push block 60, with no load, in rotational positions of zero (with eccentric 56 positioned at full vertical), 60 and 120 degrees of rotation, and under full mechanical load at 180 degrees of rotation;

FIGS. 7A, 7B, 7C and 7D respectively depict a side view of cam 50, specifically showing eccentric 56 and cylindrical section 58, corresponding to each of the rotational positions shown in FIGS. 6A, 6B, 6C and 6B;

FIGS. 8A, 8B, 8C and 8D respectively depict a right side perspective view of cam 50, specifically showing eccentric 56 and cylindrical section 58, corresponding to each of the rotational positions shown in FIGS. 6A and 7A, 6B and 7B, 6C and 7C, and 6D and 7D;

FIG. 11 depicts a side-view of an alternative embodiment of the push block, here push block 70, that provides increased deflection under mechanical load; and FIG. 12 depicts a top left perspective view of push block 70 shown in FIG. 11.

To facilitate understanding, identical reference numerals have been used, where appropriate, to designate identical or highly similar elements that are common to two or more of the figures.

DETAILED DESCRIPTION

My inventive jack assembly can be used across a wide variety of applications where a removable piece is to be mechanically locked in place between two opposing inwardly facing projections of a pair of arms extending out of a common housing, where the piece and housing abuttingly mate through complementary wedge or other appropriately shaped surfaces that provide a sufficient frictional coupling to resist relative movement therebetween. To simplify the discussion and facilitate understanding, I will illustratively describe my inventive assembly in the context of use in a mechanical materials test machine and particularly within a jaw in that machine which holds a specimen grip.

Figure 1A:
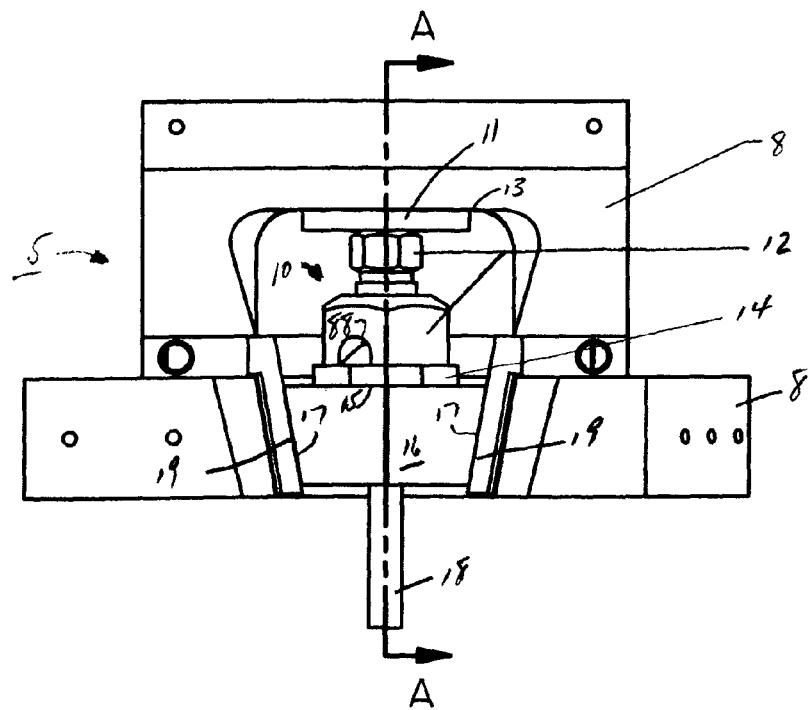
FIG. 1A depicts a side view of jaw 5 used in a mechanical testing system that contains conventional screw-type jack assembly 10.
Figure 1B:
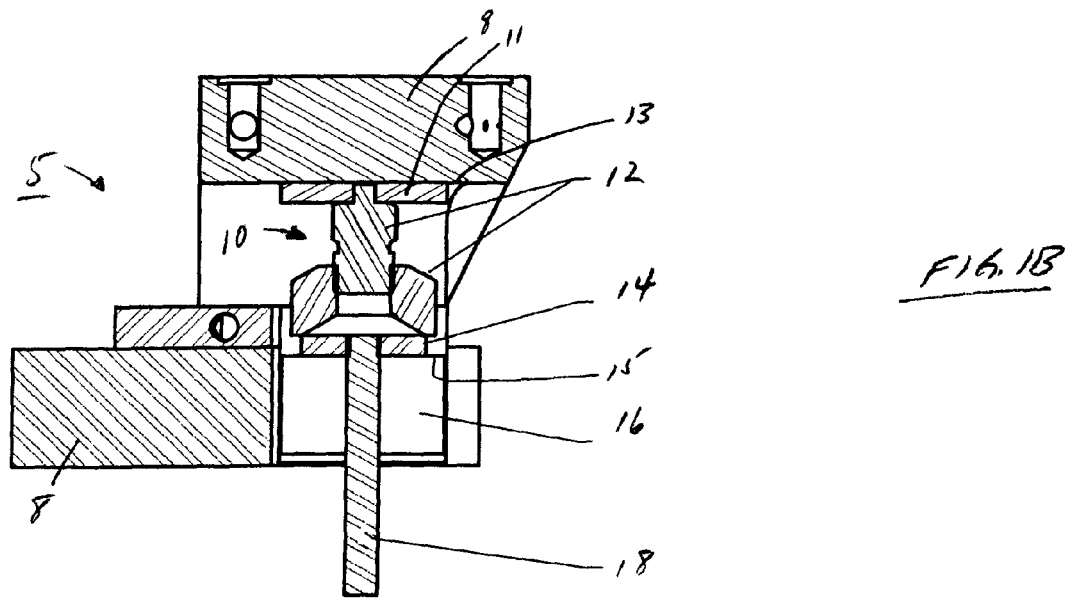
FIG. 1B depicts a cross-sectional view of jaw 5 and jack assembly 10 taken along lines A-A shown in FIG. 1A.

FIGS. 1A and 1B respectively depict a side view of jaw 5 used in a mechanical testing system and a cross-sectional view taken across lines A-A shown in FIG. 1A of this jaw. Conventionally, as shown in these two figures, specimen grip 16, which securely holds mechanical test specimen 18, is itself positioned within two wedge surfaces 19 of jaw housing 8. The grip has two inclined surfaces 17 which are complementary to and abuttingly mate with and slide against wedge surfaces 19. To hold the grip firmly in place throughout each ensuing mechanical hit during a test program, jack mechanism 10, situated between upper interior surface 13 of housing 8 and upper surface 15 of specimen grip 16, is mechanically expanded to apply a continuous force between surfaces 13 and 15 which, in turn, drives grip 16 downward and, through increasing friction between complementary surfaces 17 and 19, rigidly locks the grip into position in the jaw housing.

Jack assembly 10, which is conventional, relies on appropriately distending a screw within a nut (the screw and nut being collectively shown through reference numeral 12) and then mechanically locking the screw in position through adjustment of set screw 88 (or the like) located in the nut. A head of the screw pushes against spacer block 11. The external force for each hit, applied to a top surface of jaw housing 8, through typically a servo-controlled hydraulic piston rod (not shown but well-known), is transmitted through jack assembly 10 by jam nut 14 to grip 16. Consequently, to prevent unwanted specimen movement, jack assembly 10 must be stronger than and hence withstand mechanical forces that are greater than peak mechanical forces that are to be applied to the specimen during each hit. Furthermore, these forces, whether they be compressive, tensile or both, may well be applied to the specimen in a cyclic fashion. As such, jack assembly 10 should not loosen not only during any one hit but also during an entire test program.

Unfortunately, conventional screw-type jack assemblies may exhibit a tendency to loosen somewhat either during a hit or after a number of hits are made to the specimen. This, in turn, may permit the specimen to exhibit some unexpected movement, even if slight, during a test program which, in turn, could inject some unwanted artifact into ensuing mechanical test results.

Advantageously, my inventive jack assembly, which relies on use of a cam and resilient push block, yields considerably higher mechanical forces than a comparably sized screw and nut as used in conventional screw-type jack assemblies, and, in so doing, substantially eliminates any such tendencies of the jack assembly to loosen during a hit in a test program. Specifically, a shallow ramp formed by an external surface of the eccentric generates a considerably higher force, typically double, that which can be created by applying a equivalent tightening torque to a similar sized, conventional screw-type jack assembly. Moreover, as the cam is rotated into its top dead-center position relative to the push block, the eccentric increasingly pushes against a channel in the push block. This, in turn, causes bending moments to appear along the push block and oriented towards the cam. Since the push block is resilient relative to the cam, the bending moments will cause material surrounding the channel in the push block to deflect and elastically deform around the eccentric, and as a result, effectively lock the cam into its top dead-center position.

Consequently, the inventive jack assembly when set at its top dead-center position, by virtue of both the increased force produced through use of the cam and its deflection of the resilient push block around the eccentric, will not "back off" from that position during a mechanical test program having multiple specimen hits and thus will securely hold the specimen in a proper fixed position relative to its corresponding jaw housing throughout the test program. This, in turn, will substantially, if not totally, eliminate artifacts in mechanical test results which might otherwise arise from unwanted specimen movement during the test program.

Figure 2A:
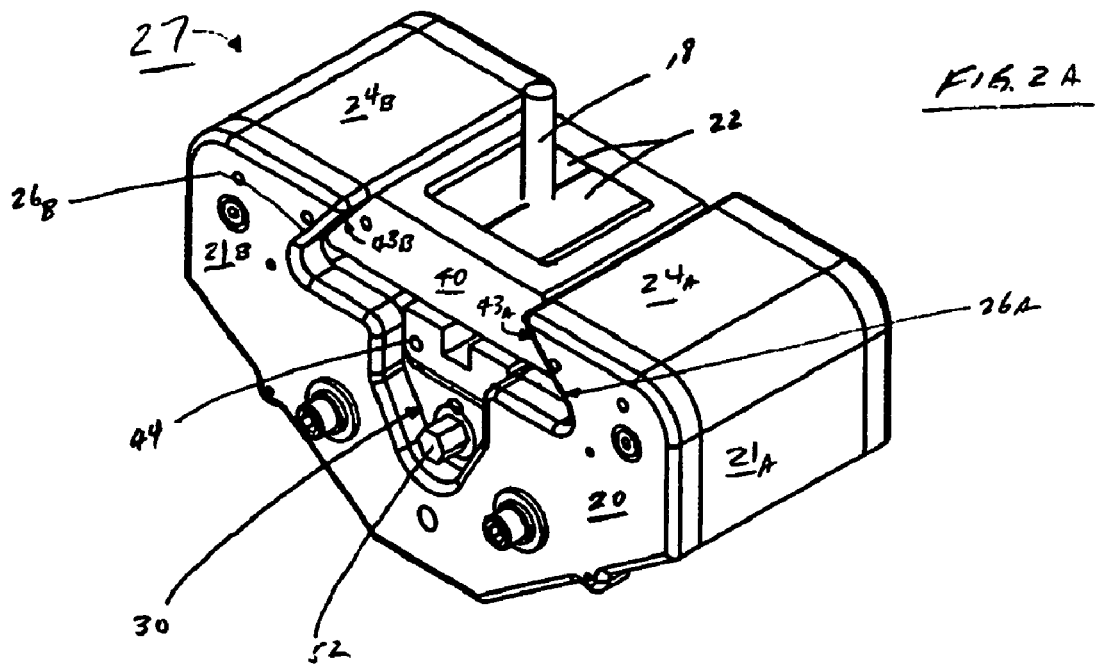
FIG. 2A depicts a right front perspective view of jaw 27 containing my inventive jack assembly and for use in, e.g., a mechanical material testing machine.
Figure 2B:
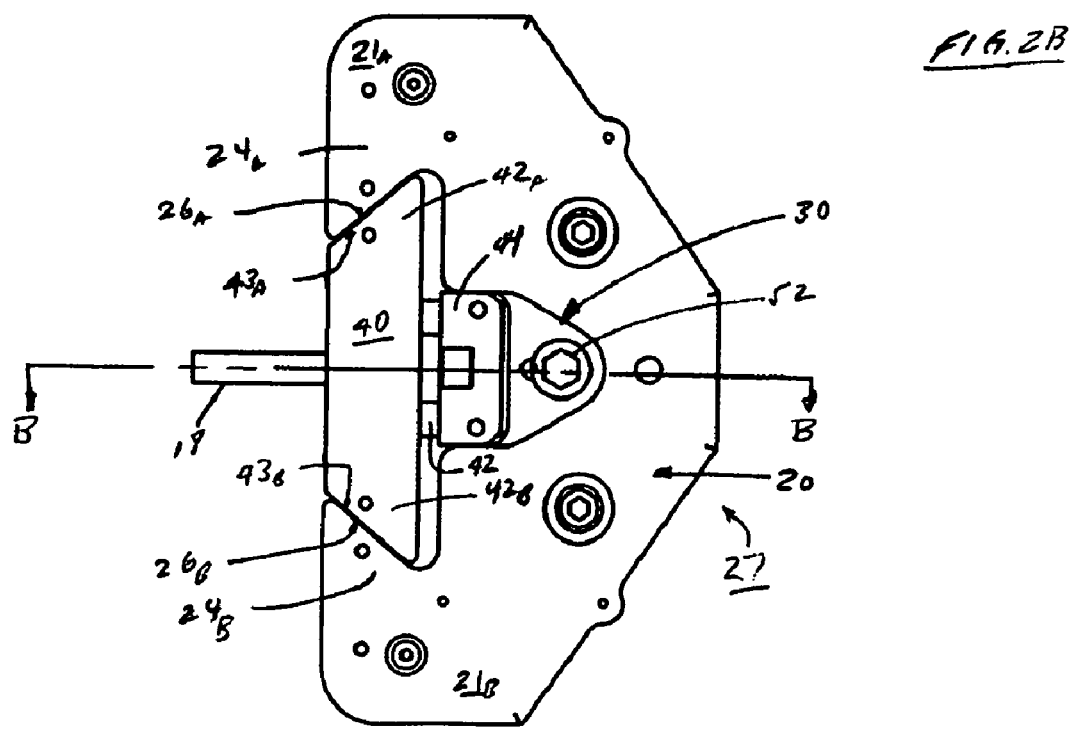
FIG. 2B depicts a side view of jaw 27 shown in FIG. 2A.

FIGS. 2A, 2B, 3, 4A and 4B depict various views of jaw 27 containing my inventive jack assembly 30. FIG. 2A depicts a right front perspective view of jaw 27 with FIG. 2B depicting a side view of jaw 27 shown in FIG. 2A and FIG. 3 depicting a cross-sectional view of that jaw taken along lines B-B shown in FIG. 2B. FIG. 4A depicts a top view of jaw 27 shown in FIG. 2A with FIG. 4B depicting a cross-sectional view of jaw 27 taken along lines C-C shown in FIG. 4A. Inventive jack assembly 30 is particularly visible in the cross-sectional views in FIGS. 3 and 4B. Nevertheless, for enhanced understanding, the reader should simultaneously refer to all these figures during the following discussion.

Inventive jack assembly 30 contains cam 50 and resilient push block 60 located within a recess in housing 20 of jaw 27 with the cam transversely extending through most of the depth (front to back) of the housing. The jaw housing is a generally V-shaped block having two outwardly extending legs $21_A$ and $21_B$. Each leg has, at its distal end, an inwardly-oriented lateral projection, specifically projections $24_A$ and $24_B$ for legs $21_A$ and $21_B$, respectively, with both projections oriented to effectively oppose each other. Each projection $24_A$ and $24_B$ has inclined face $26_A$ and $26_B$, respectively, sloping back down to the leg itself, thus forming a pair of opposing inclined faces. Specimen grip 40 is shaped in the form of two outwardly-facing wedges with a specimen situated therebetween. Each of these wedges has an upwardly inclined face, face $43_A$ and $43_B$, complementary to one of the downwardly inclined faces $26_A$ and $26_B$, respectively, on the jaw housing. The specimen grip is placed within jaw housing 20 such that each of its outwardly inclined wedge faces $43_A$ and $43_B$ abuttingly mates and slides against a corresponding inclined face $26_A$ and $26_B$, respectively, of one of the projections.

The cam is rotated, about its longitudinal axis (centerline), within housing 20 using a handle or wrench that is attached to head 52 of the cam. Head 52 can be adapted to accommodate any other suitable well-known tool than a wrench or handle, as appropriate. As the cam is rotated, an eccentric (56 as shown in FIG. 5C—which will be discussed below) of the cam pushes against push block 60 which, in turn, applies force to spacer 44. The spacer transmits the force, via jam nut 42, to specimen grip 40. Grip 40 securely contains anvil 22, here formed of a pair of wedge grips, that securely holds an end of specimen 18. This movement of the eccentric wedges the grip and specimen 18 securely in place for subsequent deforming hits. The specimen is typically a relatively short bar that is either circularly or rectilinear in cross-section.

The eccentric of the cam has a profile designed to apply full force to push block 60 in 180 degrees or less of rotation, though a different cam profile can be used to apply full force to the push block at different values of angular rotation including up to 360 degrees. Advantageously, the position of the cam in the jaw housing, namely with head 52 extending out of a side of the housing and with sufficient lateral clearance circumferentially around it, simplifies a user's task of applying torque to the cam to rotate it over that required to tighten a conventional screw-type jack assembly. For the latter and as can be appreciated from FIG. 1, a user needs to appropriately angle heads of two open-end wrenches into a fairly tight space between the legs of jaw housing 8. To tighten screw-type jack assembly 10, one of the wrench heads would mate with the screw and the other wrench head would mate with the nut. However, movement of both of the wrench heads would be confined by physical separation of those legs, thus frustrating the task of tightening that jack assembly.

Once an end of the specimen is properly secured in specimen grip 40 and the grip is properly situated within the jaw housing, jack assembly 30 is then appropriately set by rotating cam 50 from an initial position into its top dead-center position relative to push block 60. This expands (extends) the length of the jack which, in turn, exerts a sufficient continuous mechanical force against grip 40, through increasing frictional forces caused by abutting faces of wedges effectively formed by each pair of complementary inclined faces $26_A$ and $43_A$, and $26_B$ and $43_B$, of jaw housing 20 and grip 40 as they are forced towards each other, that locks the grip and therethrough specimen 18 into their proper positions in and relative to the jaw housing.

Figure 5A:
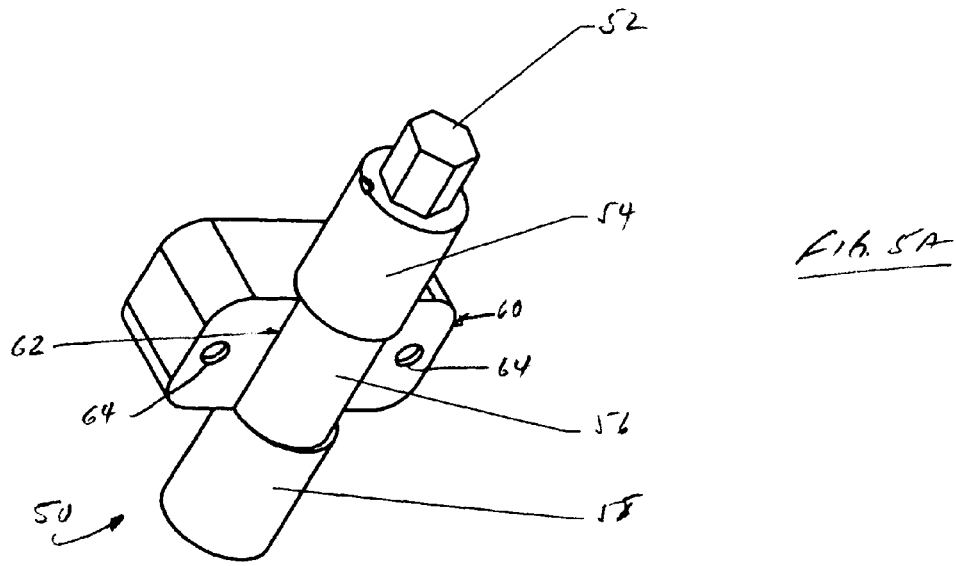
FIG. 5A depicts a bottom left perspective view of cam 50 and abutting push block 60 used in my inventive jack assembly shown in FIG. 2A.
Figure 5C:
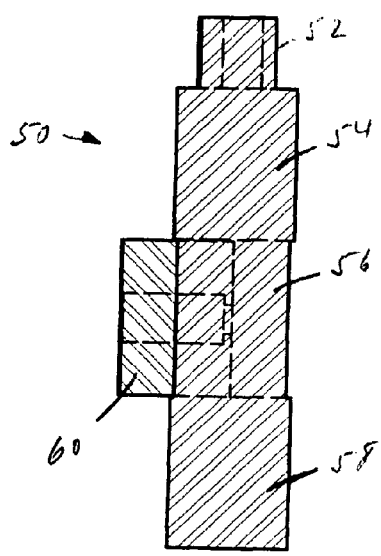
FIG. 5C depicts a cross-sectional view of cam 50, taken along lines D-D shown in FIG. 5B, with eccentric 56 therein illustrated, for ease of understanding, in an exaggerated form.
Figure 5B:
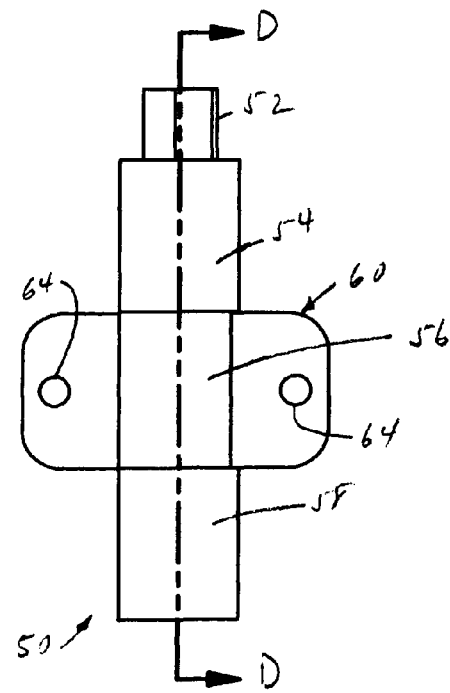
FIG. 5B depicts a top view of cam 50 shown in FIG. 5A.

Cam 50 is depicted in FIGS. 5A-5C, where FIG. 5A depicts a bottom left perspective view of cam 50 and abutting push block 60; FIG. 5B depicts a top view of cam 50 shown in FIG. 5A; and FIG. 5C depicts a cross-sectional view of the cam shown in FIG. 5A but with eccentric 56 illustrated, for ease of understanding, in an exaggerated form.

As indicated, cam 50 is formed to serially contain upper circular cylinder 54, progressive eccentric 56 which has a predefined raising rate based on its axial rotation, and lower circular cylinder 58. The eccentric is situated between push block 60 and the recess in housing 20 (with cylinders 54 and 58 providing bearing surfaces to channel 28 in housing 20), each of which, substantially along its width, has a corresponding shallow transversely extending channel (channel 62 in push block and channel 28 in housing 20) with a generally semi-circular cross-section. Cam 50 is positioned within jaw housing 20 and rotates within opposing channels 62 and 28 in both push block 60 and jaw housing 20, respectively. Push block 60 is basically a rectangular block pushing at each of its ends against spacer 44, with its channel 62 extending transversely along its mid-span. The push block is oriented perpendicular to a longitudinal axis of cam 50 and contacts, via channel 62, eccentric 56 of the cam. Push block 60 has springs connected, via screws (both the springs and screws are not specifically shown but are well-known) inserted through holes 64, to housing 20 to retract push block 60 when cam 50 is loosened, thus permitting push block 60 to follow eccentric 56.

Figure 9:
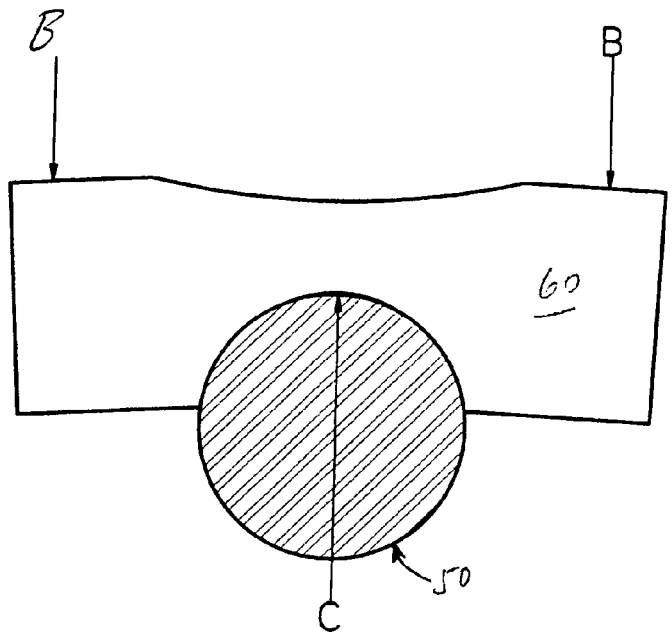
FIG. 9 shows a side view of cam 50 and abutting push block 60, under full mechanical load, with peak force applied in the direction shown by arrow C and resulting bending moments applied in the direction illustratively shown by arrows B.
Figure 10:
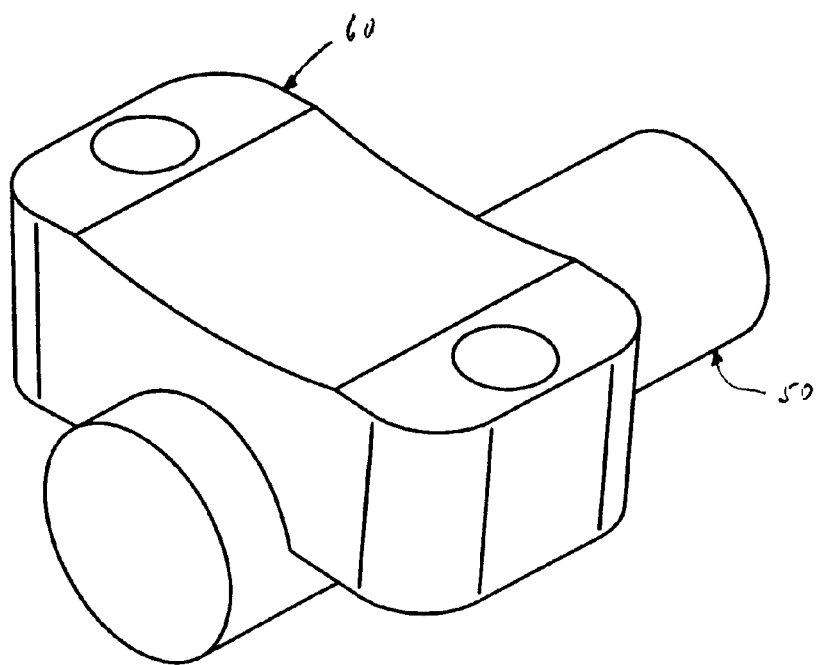
FIG. 10 depicts a top right perspective of cam 50 and push block 60 shown in FIG. 9 and under mechanical load.

As cam 50 is rotated into its top dead-center position, its eccentric 56, given its cam profile, i.e., an extent of its progressive eccentricity, will abut against and exert an increasing amount of force against a radius of push block 60 until that top dead-center position is reached at which point maximum force will be exerted by eccentric lobe 56 onto a radius of the push block. This, in turn, causes bending moments to be produced along the push block and particularly at and near each end thereof. As shown in FIG. 9, when the cam is in its top dead-center position, the eccentric generates a peak force produced by eccentric 56 at a location and in a direction shown by arrow C. Resulting bending moments produced near the ends of the block are indicated by arrows B. The push block is fabricated out of an appropriate resilient material, with a sufficiently high modulus of elasticity as compared to that of the entire cam and jaw housing, such that the bending moments applied particularly to both ends of the push block, as a result of rotation of the cam, cause channel 62 in the push block to elastically deform and increasingly and sufficiently deflect against and around eccentric 56 of the cam, thus increasingly bending around and pinching that lobe and securely locking the cam into its top dead-center position. As the deflection increases, contact surface area between the push block and a face of the eccentric lobe similarly increases which, in turn, advantageously increases a resulting frictional force between the two. Once full torque is applied to the cam to place it in its top dead-center position, the push block will not only sufficiently and maximally deflect to appropriately pinch the eccentric and lock the cam in place but also push block 60 will simultaneously act as a spring to maintain a constant force on grip 40 to also lock it, anvil 22 and specimen 18 in place in jaw 27.

The cam can be constructed in any one of several different ways. Specifically, in one implementation, upper and lower circular cylinders 54 and 58 are right cylinders. As noted above, eccentric 56 is shaped to have a profile that is progressive, i.e., applying increasing force on push block 60 as the cam is rotated. Alternatively, cam 50 could employ three right cylinders with the central cylinder having its longitudinal axis (centerline) offset from that of the other two cylinders. Preferably, cam 50 is machined or otherwise formed from a single unitary piece of material. In lieu of forming the cam from as a unitary component, the cam could be formed of three separate components, e.g., two or three cylinders and, if the former, an eccentric component, that are appropriately joined together. Ramp and eccentricity of the cam lobe or the offset of a center cylinder from the longitudinal axis of the cam can be adjusted to develop a desired amount of force applied to the push block with a known amount of input torque applied to cam head 52.

By choosing a material for push block 60 with an appropriate modulus of elasticity and appropriately sizing the length and cross-section of push block 60, the push block, as noted above, will sufficiently deflect under applied load of the eccentric lobe and will act as both a spring and a brake limiting the force applied to grip 40. As the eccentric rotates and increasingly pushes against the radius of the push block, the surface area of channel in the push block increases as a result of the deflection which, in turn, results in increased friction between the eccentric and that channel. When full torque is applied to the cam, the push block sufficiently deflects to pinch the eccentric cam and lock the cam in place. Simultaneously with that, the bending of the push block acts as a spring to maintain a constant force on grip 40.

Attention should now be focused on FIGS. 6A-6D and 7A-7D which depict cam 50 and push block 60 in side view and FIGS. 8A-8D which depict the cam alone, specifically eccentric 56 and lower cylindrical section 58, in right side perspective view, with all three figures showing the cam position for respectively zero (top dead-center), 60 and 120 degrees of rotation and all with no mechanical load on the push block, and lastly at 180 degrees of rotation and full mechanical load on the push block. For simplicity, only a small portion 20' of jaw housing 20 and against which the cam is rotating is shown.

With no force being exerted by cam 50 and as shown in FIG. 6A, channel 62 (see FIG. 5A) in push block 60 does not conform exactly to a shape of the surface of eccentric 56. The non-conformance, i.e., radial clearance, occurs on both sides 63 of a contact interface in channel 62 between the eccentric 56 and the push block and which, for ease in illustration and enhanced reader understanding, is shown in exaggerated form. Typically, the amount of the non-conformance is quite small and on the order of approximately 0.002 inches (0.0508 mm) or less, depending on the size of the eccentric and the materials used to fabricate the cam and push block.

As cam 50 increasingly rotates in a counter-clockwise direction given by arrow R in FIGS. 7A-7D, push block 60 elastically deforms to effectively bend around the eccentric at its contact interface within channel 62 (see FIG. 5A) in the push block. As this rotation occurs, from zero (FIGS. 6A, 7A and 8A) through 180 degrees (FIGS. 6D, 7D and 8D), additional force is applied in direction shown by arrow C on FIG. 9. Grip 40 resists the added force as shown by arrows B in FIG. 9. This applies a bending moment to push block 60 until that block elastically deforms even further to more closely fit the shape of eccentric 56 as shown in the succession of views in FIGS. 6A through 6D. The initial shape of the non-conformance between eccentric 56 and push block 60 is set to appropriately accommodate eventual deflection, here being elastic deformation, of the push block at maximal extension of eccentric 56, i.e., at the top dead-center position of the cam shown in FIGS. 6D, 7D and 8D.

Now, as the cam is rotated into its top dead-center position and applies increasing force to push block 60, the contact surface area between the push block and eccentric increases as a result of the deflection which, in turn, increases the friction along that surface area thus further preventing the cam from loosening or backing off from its tightened position. This increasing contact area allows both the cam and push block to handle the larger force without either component undergoing plastic deformation which, if it were to occur, would permanently damage that component and thus render the jack assembly ineffective. When the cam is positioned to apply maximum force, all or a substantial part of the cam surface will be in contact with the push block as shown in FIG. 9.

The resiliency and size of the push block can be selected such that push block 60, when it is fully deflected, actually pinches cam 50 in place to prevent the latter from loosening. Furthermore, the push block can be designed to impart a specific, predefined amount of force to specimen grip 40 when the cam stops turning due to the pinch effect of the push block when the cam is locked in place. The amount through which the cam can be turned becomes limited by the pinch effect that occurs on the sides of the eccentric. Hence, the inventive jack assembly effectively self-regulates how much force can be applied by the cam and push block. Moreover, it locks the cam in position without the need to rotate the cam "over-center" as most conventional cam-actuated devices require in order to lock their cams in place. Once the test program is finished, a wrench is used to reverse the rotation of cam 50 and thus loosen the cam which, in turn, removes the force previously holding push block 60 and specimen grip 40 in place.

Illustratively, the cam is formed of three right cylinders and sized such that upper and lower cylinders 54 and 58, respectively, and eccentric 56 are each 1" (approximately 2.5 cm) in length. Cylinders 54 and 58, which are coaxial with a centerline of the cam, each has a diameter of 0.75" (approximately 1.9 cm). Eccentric 56 has a diameter of 0.7" (approximately 1.8 cm) and a longitudinal axis (centerline) offset from that of both cylinders 54 and 58 by 0.025" (approximately 0.6 mm). Hence, the eccentric provides a resulting throw of 0.05" (approximately 1.3 mm) ±0.025" of the centerline of the cam. Push block 60 is 1" (approximately 2.5 cm) in both height and thickness and 1.9" in length (approximately 4.8 cm) and has a radius of channel 62 of 0.704" (approximately 1.788 cm). Both the push block and the cam are fabricated from 17-4 PH H900 stainless steel having, approximately, a yield strength of 183,000 PSI; a modulus of elasticity of 28600 Ksi; and a Rockwell hardness (hardness RC) of 44.

The design of push block 60 can be varied, as needed, to change the amount of deflection that occurs when the force is applied by the eccentric to the push block. As shown in the side view in FIG. 11 of an alternate embodiment of push block 60, the thickness of push block 70, particularly in its central section and indicated by a dimension between lines labeled A, can be changed to adjust the amount of deflection produced under load. By reducing the thickness of the central portion, increased deflection can occur along channel 62. FIG. 12 depicts a top left perspective view of push block 70 shown in FIG. 11. Moreover, the material used to manufacture the push block and hence its modulus of elasticity can also be changed to adjust the amount of ensuing deflection. The material is chosen to provide a push block that can bend as desired under a full load but yet still return to its original shape when the load is removed. Design choices for the push block are also governed, in part, by the peak force applied to jaw 27, the cross-sectional area of the push block and an effective length of the push block.

While the inventive jack assembly described above and illustrated in the figures has the cam and push block integrated into jaw housing 20 itself, the jack assembly can easily be manufactured as a separate assembly with the cam and the push block both contained within a separate housing that is positioned within a jaw housing in order to provide jacking force against an associated wedge grip. Such an approach would likely be suitable for constructing a direct replacement for the conventional screw-type jack assembly discussed above and shown in FIGS. 1A and 1B.

Although a single preferred embodiment and various modifications of components used therein which incorporate the teachings of my present invention have been shown and described in considerable detail herein, those skilled in the art can readily devise many other varied embodiments and modifications that still incorporate these teachings.

I claim:

1. Apparatus for use in a materials testing machine for securely holding a specimen grip in a fixed position relative to a jaw housing, the apparatus comprising:

the jaw housing containing the specimen grip, the grip having two external opposing inclined faces, each of the faces abutting against a corresponding one of two complementary interior faces of the jaw housing, the two complementary faces and a bottom interior surface of the housing collectively forming a cavity in the jaw housing which accommodates the specimen grip; and a cam jack situated in a recess in the housing below the cavity, wherein the cam jack abuttingly engages with an underside of the specimen grip and an opposing interior surface of the housing and generates an increasing mechanical force which moves the faces of the specimen grip against the complementary faces of the housing so as to frictionally lock the specimen grip into the fixed position in the jaw housing, the cam jack having:

a cylindrical cam having an eccentric, with a contact surface having a predefined raising rate, the cam being oriented for rotational movement about a longitudinal axis thereof; and a resilient push block having first and second opposing surfaces and oriented transverse to the longitudinal axis of the cam, the first surface of the push block oriented to transmit the mechanical force to the underside of the specimen grip, and the second surface of the push block having a first channel formed therein with a predefined shape and against which the eccentric rotatingly abuts, with the push block also having and first and second end portions situated between the first and second opposing surfaces and oppositely and transversely extending beyond the cam; and wherein, the eccentric, as a result of the rotational movement of the cam in the first channel, to a predefined angular position, causes the push block to apply said mechanical force, through the first surface of the push block, to the specimen grip to lock the specimen grip in the fixed position and also causes bending moments to appear in the first and second end portions of the push block which, in turn, cause the first channel to undergo increasing elastic deformation such that a contact surface of the first channel increasingly deflects around the contact surface of the eccentric until said predefined angular position is reached and thereby, through increased friction occurring between the contact surface of the eccentric and the contact surface of the first channel as a result of the deflection, prevents the cam from rotating from said predefined angular position.

2. The apparatus in claim 1 wherein the cam is also in rotational abutment with a contact surface of a second channel formed in the opposing interior surface of the jaw housing, the second channel having a substantially semi-circular cross-sectional shape.

3. The apparatus recited in claim 2 wherein the predefined angular position is a top dead-center rotational position of the cam relative to the push block.

4. The apparatus recited in claim 3 wherein the cam comprises a lower cylinder, the eccentric and an upper cylinder, with the upper and lower cylinders being right cylinders and coaxially aligned with the longitudinal axis of the cam.

5. The apparatus recited in claim 4 wherein the eccentric comprises a right cylinder having a centerline that is offset by a predefined distance from the longitudinal axis of the cam.

6. The apparatus recited in claim 4 wherein the eccentric is coaxial with the cam and has a predefined progressive profile.

7. The apparatus recited in claim 4 wherein the cam is adapted for manual rotation into the top dead-center position by a user of the apparatus.

8. The apparatus recited in claim 4 wherein, when no force is being applied by the eccentric to the push block, the first channel has a substantially circular cross-sectional shape.

9. The apparatus recited in claim 8 wherein, when no force is being applied by the eccentric to the push block, a predefined amount of radial clearance exists between the contact surface of the first channel and the contact surface of the eccentric.

10. The apparatus recited in claim 9 wherein, as the cam is rotated into the predefined angular position, the contact surface of the push block which abuts against the contact surface of the eccentric is increasingly deformed to bend around and conform to the contact surface of the eccentric until the top dead-center position is reached at which the contact surface of the push block conforms to and pinches against the contact surface of the eccentric effectively locking the cam in the top dead-center position.

11. The apparatus recited in claim 10 wherein the push block has a central area having a reduced thickness relative to the first and second end portions of the push block so as to provide increased deflection of the contact surface of the first channel against the contact surface of the eccentric when the cam is rotated to the top dead-center position.

12. Apparatus for a cam jack for use in a materials testing machine for securely holding a specimen grip in fixed position relative to the jaw housing, the testing machine having a jaw housing containing the specimen grip, the grip having two external opposing inclined faces, each of the faces abutting against a corresponding one of two complementary interior faces of the jaw housing, the two complementary faces and a bottom interior surface of the housing collectively forming a cavity in the jaw housing which accommodates the specimen grip; and the cam jack situated in a recess in the housing below the cavity, wherein the cam jack abuttingly engages with an underside of the specimen grip and an opposing interior surface of the housing and generates an increasing mechanical force which moves the faces of the specimen grip against the complementary faces of the housing so as to frictionally lock the specimen grip into the fixed position in the jaw housing, the cam jack having:

a cylindrical cam having an eccentric, with a contact surface having a predefined raising rate, the cam being oriented for rotational movement about a longitudinal axis thereof; and a resilient push block having first and second opposing surfaces and oriented transverse to the longitudinal axis of the cam, the first surface of the push block oriented to transmit the mechanical force to the underside of the specimen grip, and the second surface of the push block having a first channel formed therein with a predefined shape and against which the eccentric rotatingly abuts, with the push block also having and first and second end portions situated between the first and second opposing surfaces and oppositely and transversely extending beyond the cam; and wherein, the eccentric, as a result of the rotational movement of the cam in the first channel, to a predefined angular position, causes the push block to apply said mechanical force, through the first surface of the push block, to the specimen grip to lock the specimen grip in the fixed position and also causes bending moments to appear in the first and second end portions of the push block which, in turn, cause the first channel to undergo increasing elastic deformation such that a contact surface of the first channel increasingly deflects around the contact surface of the eccentric until said predefined angular position is reached and thereby, through increased friction occurring between the contact surface of the eccentric and the contact surface of the first channel as a result of the deflection, prevents the cam from rotating from said predefined angular position.

13. The apparatus recited in claim 12 wherein the predefined angular position is a top dead-center rotational position of the cam relative to the push block.

14. The apparatus recited in claim 13 wherein the cam comprises a lower cylinder, the eccentric and an upper cylinder, with the upper and lower cylinders being right cylinders and coaxially aligned with the longitudinal axis of the cam.

15. The apparatus recited in claim 14 wherein the eccentric comprises a right cylinder having a centerline that is offset by a predefined distance from the longitudinal axis of the cam.

16. The apparatus recited in claim 14 wherein the eccentric is coaxial with the cam and has a predefined progressive profile.

17. The apparatus recited in claim 14 wherein the cam is adapted for manual rotation into the top dead-center position by a user of the apparatus.

18. The apparatus recited in claim 14 wherein, when no force is being applied by the eccentric to the push block, the first channel has a substantially circular cross-sectional shape.

19. The apparatus recited in claim 18 wherein, when no force is being applied by the eccentric to the push block, a predefined amount of radial clearance exists between the contact surface of the first channel and the contact surface of the eccentric.

20. The apparatus recited in claim 19 wherein, as the cam is rotated into the predefined angular position, the contact surface of the push block which abuts against the contact surface of the eccentric is increasingly deformed to bend around and conform to the contact surface of the eccentric until the top dead-center position is reached at which the contact surface of the push block conforms to and pinches against the contact surface of the eccentric effectively locking the cam in the top dead-center position.

21. The apparatus recited in claim 20 wherein the push block has a central area having a reduced thickness relative to the first and section end portions of the push block so as to provide increased deflection of the contact surface of the first channel against the contact surface of the eccentric when the cam is rotated to the top dead-center position.

22. A material testing machine having:
a jaw housing containing a specimen grip, for securely holding the specimen grip in a fixed position relative to the jaw housing, the grip having two external opposing inclined faces, each of the faces abutting against a corresponding one of two complementary interior faces of the jaw housing, the two complementary faces and a bottom interior surface of the housing collectively forming a cavity in the jaw housing which accommodates the specimen grip; and
a cam jack situated in a recess in the housing below the cavity, wherein the cam jack abuttingly engages with an underside of the specimen grip and an opposing interior surface of the housing and generates an increasing mechanical force which moves the faces of the specimen grip against the complementary faces of the housing so as to frictionally lock the specimen grip into the fixed position in the jaw housing, the cam jack having:
a cylindrical cam having an eccentric, with a contact surface having a predefined raising rate, the cam being oriented for rotational movement about a longitudinal axis thereof; and
a resilient push block having first and second opposing surfaces and oriented transverse to the longitudinal axis of the cam, the first surface of the push block oriented to transmit the mechanical force to the underside of the specimen grip, and the second surface of the push block having a first channel formed therein with a predefined shape and against which the eccentric rotatingly abuts, with the push block also having and first and second end portions situated between the first and second opposing surfaces and oppositely and transversely extending beyond the cam; and
wherein, the eccentric, as a result of the rotational movement of the cam in the first channel, to a predefined angular position, causes the push block to apply said mechanical force, through the first surface of the push block, to the specimen grip to lock the specimen grip in the fixed position and also causes bending moments to appear in the first and second end portions of the push block which, in turn, cause the first channel to undergo increasing elastic deformation such that a contact surface of the first channel increasingly deflects around the contact surface of the eccentric until said predefined angular position is reached and thereby, through increased friction occurring between the contact surface of the eccentric and the contact surface of the first channel as a result of the deflection, prevents the cam from rotating from said predefined angular position.

23. The apparatus in claim 22 wherein the cam is also in rotational abutment with a contact surface of a second channel formed in the opposing interior surface of the jaw housing, the second channel having a substantially semi-circular cross-sectional shape.

24. The apparatus recited in claim 23 wherein the predefined angular position is a top dead-center rotational position of the cam relative to the push block.

25. The apparatus recited in claim 24 wherein the cam comprises a lower cylinder, the eccentric and an upper cylinder, with the upper and lower cylinders being right cylinders and coaxially aligned with the longitudinal axis of the cam.

26. The apparatus recited in claim 25 wherein the eccentric comprises a right cylinder having a centerline that is offset by a predefined distance from the longitudinal axis of the cam.

27. The apparatus recited in claim 25 wherein the eccentric is coaxial with the cam and has a predefined progressive profile.

28. The apparatus recited in claim 25 wherein the cam is adapted for manual rotation into the top dead-center position by a user of the apparatus.

29. The apparatus recited in claim 25 wherein, when no force is being applied by the eccentric to the push block, the first channel has a substantially circular cross-sectional shape.

30. The apparatus recited in claim 29 wherein, when no force is being applied by the eccentric to the push block, a predefined amount of radial clearance exists between the contact surface of the first channel and the contact surface of the eccentric.

31. The apparatus recited in claim 30 wherein, as the cam is rotated into the predefined angular position, the contact surface of the push block which abuts against the contact surface of the eccentric is increasingly deformed to bend around and conform to the contact surface of the eccentric until the top dead-center position is reached at which the contact surface of the push block conforms to and pinches against the contact surface of the eccentric effectively locking the cam in the top dead-center position.

32. The apparatus recited in claim 31 wherein the push block has a central area having a reduced thickness relative to the first and second end portions of the push block so as to provide increased deflection of the contact surface of the first channel against the contact surface of the eccentric when the cam is rotated to the top dead-center position.

33. A method for use in a materials testing machine, the machine having:
- a jaw housing containing the specimen grip, for securely holding the specimen grip in a fixed position relative to the jaw housing, the grip having two external opposing inclined faces, each of the faces abutting against a corresponding one of two complementary interior faces of the jaw housing, the two complementary faces and a bottom interior surface of the housing collectively forming a cavity in the jaw housing which accommodates the specimen grip; and
- a cam jack situated in a recess in the housing below the cavity, wherein the cam jack abuttingly engages with an underside of the specimen grip and an opposing interior surface of the housing and generates an increasing mechanical force which moves the faces of the specimen grip against the complementary faces of the housing so as to frictionally lock the specimen grip into the fixed position in the jaw housing, the cam jack having:
    - a cylindrical cam having an eccentric, with a contact surface having a predefined raising rate, the cam being oriented for rotational movement about a longitudinal axis thereof; and
    - a resilient push block having first and second opposing surfaces and oriented transverse to the longitudinal axis of the cam, the first surface of the push block oriented to transmit the mechanical force to the underside of the specimen grip, and the second surface of the push block having a first channel formed therein with a predefined shape and against which the eccentric rotatingly abuts, with the push block also having and first and second end portions situated between the first and second opposing surfaces and oppositely and transversely extending beyond the cam;

wherein the method comprises the steps of:
- situating, with the cam residing at an initial angular position, the specimen grip within the cavity such that the external faces of the specimen grip abuttingly engage with the complementary faces of the jaw housing; and
- at the conclusion of the situating step, rotating the cam from the initial angular position to a predefined angular position so that the eccentric, as a result of the rotational movement of the cam, causes the push block to apply said mechanical force, through the first surface of the push block, to the specimen grip to lock the specimen grip in the fixed position and also causes bending moments to appear in the first and second end portions of the push block which, in turn, cause the first channel to undergo increasing elastic deformation such that a contact surface of the first channel increasingly deflects around the contact surface of the eccentric until said predefined angular position is reached and thereby, through increased friction occurring between the contact surface of the eccentric and the contact surface of the first channel as a result of the deflection, prevents the cam from rotating from said predefined angular position.

34. The method in claim 33 wherein the cam is also in rotational abutment with a contact surface of a second channel formed in the opposing interior surface of the jaw housing, the second channel having a substantially semi-circular cross-sectional shape.

35. The method recited in claim 34 wherein the predefined angular position is a top dead-center rotational position of the cam relative to the push block.

36. The method recited in claim 35 wherein the rotating step comprises the step, performed by a user of the material testing machine, of manually rotating the cam into the top dead-center position.

37. The apparatus in claim 12 wherein the cam is also in rotational abutment with a contact surface of a second channel formed in the opposing interior surface of the jaw housing, the second channel having a substantially semi-circular cross-sectional shape.

* * * * *